(12) United States Patent
Takahashi et al.

(10) Patent No.: US 8,422,631 B2
(45) Date of Patent: Apr. 16, 2013

(54) RADIATION THERAPY PLANNING APPARATUS AND RADIATION THERAPY PLANNING METHOD

(75) Inventors: Kunio Takahashi, Hiroshima (JP); Kenji Takayama, Hiroshima (JP); Yuki Miyabe, Kyoto (JP); Yuichiro Narita, Kyoto (JP); Takashi Mizowaki, Kyoto (JP)

(73) Assignees: Mitsubishi Heavy Industries, Ltd., Tokyo (JP); Kyoto University, Kyoto (JP)

( * ) Notice: Subject to any disclaimer, the term of this patent is extended or adjusted under 35 U.S.C. 154(b) by 318 days.

(21) Appl. No.: 12/746,572

(22) PCT Filed: Dec. 5, 2008

(86) PCT No.: PCT/JP2008/072178
§ 371 (c)(1),
(2), (4) Date: Sep. 21, 2010

(87) PCT Pub. No.: WO2009/072618
PCT Pub. Date: Jun. 11, 2009

(65) Prior Publication Data
US 2011/0044429 A1  Feb. 24, 2011

(30) Foreign Application Priority Data

Dec. 7, 2007  (JP) ................................. 2007-317653

(51) Int. Cl.
*A61N 5/10* (2006.01)
(52) U.S. Cl.
USPC .......................................................... 378/65
(58) Field of Classification Search .................... 378/62, 378/65, 108
See application file for complete search history.

(56) References Cited

U.S. PATENT DOCUMENTS

2006/0074292 A1  4/2006  Thomson et al.
2007/0165779 A1*  7/2007  Chen et al. ....................... 378/65
(Continued)

FOREIGN PATENT DOCUMENTS

CN  101011617  8/2007
EP  1 832 313  9/2007
(Continued)

OTHER PUBLICATIONS

International Search Report issued Feb. 3, 2009 in International (PCT) Application No. PCT/JP2008/072178.

(Continued)

*Primary Examiner* — Irakli Kiknadze
(74) *Attorney, Agent, or Firm* — Wenderoth, Lind & Ponack, L.L.P.

(57) ABSTRACT

A radiation therapy planning apparatus includes a three-dimensional data collection part collecting three-dimensional data representing a plurality of positions where a plurality of portions of a subject are positioned, a marker position measurement part measuring a motion of a marker, and a dose calculation part calculating, when the subject is irradiated with therapeutic radiation changing on the basis of the motion of the subject, the dose of the therapeutic radiation with which each of the plurality of portions is irradiated, based on the motion and the three-dimensional data. The radiation therapy planning apparatus thus constructed can calculate the dose of the therapeutic radiation with which each of the respective portions of the subject is irradiated, more accurately, and reduce the dose of radiation with which the subject is irradiated in calculating the motions of the plurality of portions of the subject.

25 Claims, 9 Drawing Sheets

U.S. PATENT DOCUMENTS

2007/0195929 A1* 8/2007 Ruchala et al. .................. 378/65
2007/0211857 A1 9/2007 Urano et al.

FOREIGN PATENT DOCUMENTS

| | | |
|---|---|---|
| JP | 8-89589 | 4/1996 |
| JP | 2001-327514 | 11/2001 |
| JP | 2002-186678 | 7/2002 |
| JP | 3746747 | 4/2004 |
| JP | 2006-21046 | 1/2006 |
| JP | 2006-51064 | 2/2006 |
| JP | 2006-180910 | 7/2006 |
| JP | 2007-236760 | 9/2007 |
| JP | 2008-514352 | 5/2008 |
| WO | 2006/039009 | 4/2006 |

OTHER PUBLICATIONS

Supplementary European Search Report issued Jul. 18, 2011 in corresponding European Patent Application No. 08857504.8.
Chinese Office Action mailed Sep. 3, 2012 in corresponding Chinese Patent Application No. 200880116466.0.

* cited by examiner

RADIATION THERAPY PLANNING APPARATUS AND RADIATION THERAPY PLANNING METHOD

BACKGROUND OF THE INVENTION

I. Technical Field

The present invention relates to a radiation therapy planning apparatus and a radiation therapy planning method, and more particularly to a radiation therapy planning apparatus and a radiation therapy planning method which are used for creating a therapeutic plan of radiation therapy for treating a patient by irradiating the affected part with radiation.

II. Description of the Related Art

A radiation treatment is known in the art which treats a patient by irradiating an affected part (a tumor) with therapeutic radiation. An example of the therapeutic radiation is an X-ray. Known radiation therapies include irradiation of a wider range than the affected part in view of the magnitude of the movement of the affected part, the gated irradiation, the moving body tracking irradiation, and the intensity modulated radiation therapy (IMRT). The gated irradiation is a method for irradiating the therapeutic radiation and stopping the irradiation on the basis of the movement of the observed patient. Such gated irradiation suffers from a drawback of an increased treatment time, since the irradiation of the radiation is performed only during a specified phase of breathing, for example, which puts a strain on the patient and necessitates an improvement in the efficiency of the medical treatment. The tracking irradiation is a method for observing the position of the affected part and irradiating the position with therapeutic radiation. The IMRT is a radiation method which involves varying the amount of the radiation with which each portion of the patient is irradiated through combining a plurality of beams, to thereby carry out a radiation therapy suitable for the shape of the tumor. The radiation therapy is desired to have a high therapeutic effect and desired to be evaluated more adequately.

A 4D-CT which allows obtaining a three-dimensional image for each breathing phase is known in the art. A four-dimensional radiation therapy planning apparatus for carrying out an estimation of dose distribution to a moving target by using such three-dimensional images is developed, and a radiation therapy system which is able to change the direction of X-ray irradiation in real time and to track the target is known in the art. Moreover, a technique is known in the art which allows checking positions of internal organs in real time by combining not only the X-ray imaging but also the MRI apparatus with the radiation therapy apparatus. Furthermore, an adaptive therapy is known in the art in which the therapy is implemented while being modified on the basis of the movement of these organs, a change of body contour, and each therapy result.

A four-dimensional therapy planning apparatus is known in the art which carries out the planning by using tomography images of the 4D-CT according to a plurality of phases of the breathing. The four-dimensional therapy planning apparatus first obtains a plurality of tomography images corresponding to the respective phases of the breathing (for example, eight phases) by using the 4D-CT. The four-dimensional therapy planning apparatus then constructs a correspondence relationship between the shape of organ deforming along with the breathing and the breathing phases. When an inputted therapy plan is carried out, the four-dimensional therapy planning apparatus calculates the radiation dose with which the organ extracted from the tomography image of each phase is irradiated. The four-dimensional therapy planning apparatus calculates the dose with which the organ is irradiated by summing the doses in the respective phases on the basis of the correspondence relationship. Generally, the radiation exposure from 4D-CT acquisition is large, and the temporal resolution of 4D-CT images is low. It is desired that the dose of the X-ray with which the patient is irradiated is reduced and that the dose with which the patient is irradiated in the radiation therapy is calculated more accurately.

Disclosed in Japanese Patent Application Publication No. H08-089589 is a display method used for radiation therapy planning which can create a therapy plan in view of a plurality of conditions of a subject moving in the irradiation area. The display method used for the radiation therapy planning is characterized by including steps of: reading a series of CT images obtained in each of a plurality of different conditions to set an irradiation area, an irradiation-free area and a radiation therapy parameter; creating projection shapes for respective different conditions by projecting the irradiation area and the irradiation-free area on the irradiation field on the basis of the same geometric conditions as those of the irradiation; superimposing the projection shapes of the irradiation areas created in each of a plurality of different conditions at each of respective irradiation angles; creating an irradiation field shape at each of the respective irradiation angles on the basis of the irradiation area superimposed at each of the respective irradiation angles and the set radiation therapy parameter; and superimposing the superimposed irradiation area and the created irradiation field shape at each of the respective irradiation angles and displaying them.

Disclosed in Japanese Patent Application Publication No. 2001-327514 is a radiation therapy planning apparatus which can carry out the setting accurately in view of the position and shape of the affected part which change in accordance with the breathing and heartbeats of a subject to achieve more precise and accurate radiation therapy. The radiation therapy planning apparatus, which creates a plan of the radiation therapy on the basis of an image obtained by irradiating an X-ray to the subject, is characterized by including: image generation means adapted to generate a plurality of images according to difference of phase data of the subject; input means adapted to set and input to the images a target shape to an objective portion existing on the image; and image display means adapted to superimpose and display a plurality of images and the target shapes according to difference of said phase data and said target shape.

Radiation treatment is known in the art which treats a patient by irradiating an affected part (a tumor) with therapeutic radiation. An example of the therapeutic radiation is an X-ray. Known radiation therapies include irradiation of a wider range than the affected part in view of the magnitude of the movement of the affected part, the gated irradiation, the moving body tracking irradiation, and the intensity modulated radiation therapy (IMRT). The gated irradiation is a method for irradiating the therapeutic radiation and stopping the irradiation on the basis of the movement of the observed patient. Such gated irradiation suffers from a drawback of an increased treatment time, since the irradiation of the radiation is performed only during a specified phase of breathing, for example, which puts a strain on the patient and necessitates an improvement in the efficiency of the medical treatment. The tracking irradiation is a method for observing the position of the affected part and irradiating the position with therapeutic radiation. The IMRT is a radiation method which involves varying the amount of the radiation with which each portion of the patient is irradiated through combining a plurality of beams, to thereby carry out a radiation therapy suitable for the shape of the tumor. The radiation therapy is desired to have a high therapeutic effect and desired to be evaluated more adequately.

Disclosed in Japanese Patent Application Publication No. 2006-021046A is a radiation therapy apparatus which achieves real time monitoring of the state of the therapeutic field even during therapeutic irradiation. The radiation therapy apparatus includes: an O-shaped gantry; an irradiation head for irradiating a therapeutic radiation to a therapeutic field of a subject, the irradiation head being movably provided for said O-shaped gantry; an X-ray source for irradiating a diagnostic X-ray to said therapeutic field of said subject, the X-ray source being movably provided for the O-shaped gantry; and sensor arrays for detecting a transmission X-ray of said diagnostic X-ray transmitting through said subject to output diagnostic image data, the sensor arrays being movably provided for said O-shaped gantry, wherein the sensor arrays are disposed at symmetrical positions across the irradiation head and move on said O-shaped gantry in synchronization with movement of the irradiation head, and the X-ray source moves in synchronization with movement of said sensor arrays.

Disclosed in Japanese Patent Application Publication No. 2007-236760A is a radiation therapy apparatus control device that irradiates a portion of a moving subject with radiation, more accurately. The radiation therapy apparatus control device controls a radiation therapy apparatus including: a therapeutic radiation irradiation device for irradiating a portion of a subject with therapeutic radiation; a movement detection device for detecting movement of said subject; and a drive device for moving said therapeutic radiation irradiation device with respect to said subject; the radiation therapy apparatus control device includes: an affected part position database for correlate movement aggregation with position aggregation; a movement collection part for collecting the movement from the movement detection device; and an irradiation position control part for moving the therapeutic radiation irradiation device by using said drive device so that the position corresponding to said movement of said position aggregation can be irradiated with the therapeutic radiation.

Disclosed in Japanese Translation of PCT Application No, 2008-514352 is a reliable and efficient method for dynamically tracking a moving target. The method that dynamically tracks one or more targets in an anatomical region including one or more reference structures and gives a therapeutic radiation said target during movement of said anatomical region, includes steps of: detecting in real time an existence position of said target with respect to said reference structure in said moving anatomical region; and generating a radiation dose distribution to prescribe a desired dose of said therapeutic radiation to be given in real time said target in the moving anatomical region, wherein said radiation dose distribution takes into account deformation of said anatomical region in said movement.

SUMMARY OF THE INVENTION

An object of the present invention is to provide a radiation therapy planning apparatus that evaluates a therapy plan of a radiation therapy more appropriately.

Another object of the present invention is to provide a radiation therapy planning apparatus that reduces a burden of creating the therapy plan of a radiation therapy.

Further another object of the present invention is to provide a radiation therapy planning apparatus that calculates dose of a radiation with which a risk portion is irradiated, more accurately.

Further another object of the present invention is to provide a radiation therapy planning apparatus that creates a therapy plan in which the dose of radiation with which the risk portion is irradiated is reduced.

Further another object of the present invention is to provide a radiation therapy planning method in which the dose of radiation with which a risk portion is irradiated is reduced.

Further another object of the present invention is to provide a radiation therapy apparatus control device and an irradiation method in which the dose of radiation with which a risk portion is irradiated is reduced.

A radiation therapy planning apparatus according to the present invention is provided with: a three-dimensional data collection part collecting three-dimensional data representing a plurality of positions where a plurality of portions of a subject are positioned in a stationary state or a state at a specific timing; a marker position measurement part sequentially measuring a specific position of a specific portion out of the plurality of portions which changes in synchronization with a periodic movement of the subject; a position calculation part calculating time-dependent specific positions of the plurality of portions based on the three-dimensional data collected by the three-dimensional data collection part and on the time-dependent specific position measured by the marker position measurement part; and a dose calculation part calculating a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions calculated by the position calculation part.

The radiation therapy planning apparatus according to the present invention can be configured by simple devices, and can estimate the dose of the therapeutic radiation with which the plurality of portions, whose positions change in synchronization with the periodic motion of the subject, are irradiated, more accurately and rapidly. Moreover, the radiation therapy planning apparatus according to the present invention can reduce the dose of radiation with which the subject is irradiated in calculating the motions of the plurality of portions of the subject in comparison with a case of calculating the motions of the plurality of portions of the subject on the basis of data measured by the 4D-CT. Furthermore, creating and correcting the radiation therapy plan by using data of dose of the radiation are useful not only for secure irradiation of the affected part with radiation and for irradiation with radiation keeping away from a risky portion but also for an accurate radiation therapy further reducing a radiation dose with which a portion other than the affected part is irradiated.

The radiation therapy planning apparatus according to the present invention further includes: an irradiation recipe collection part which includes an irradiation recipe input device to which an irradiation recipe for irradiating the therapeutic radiation controlled so as to change based on the periodic motion of the subject is inputted, and collects the irradiation recipe inputted to the irradiation recipe input device. In this case, the dose calculation part calculates a dose of the therapeutic radiation in a case of being controlled in accordance with the irradiation recipe which is inputted to the irradiation recipe input device and collected by the irradiation method collection part. That is, the radiation therapy planning apparatus according to the present invention can calculate a dose of the therapeutic radiation with which each of a plurality of portions is irradiated in carrying out an arbitrary irradiation method.

The radiation therapy planning apparatus according to the present invention further includes a phase detection part detecting a plurality of times corresponding to a plurality of phases of the periodic motion of the subject. On this occasion, the position of the specific portion measured by the marker position measurement part indicates the position at the times detected by the phase detection part.

The radiation therapy planning apparatus according to the present invention includes a selected portion input device to which data to select any one of the plurality of portions is inputted. On this occasion, the dose calculation part further calculates a dose of the radiation with which the selected portion of the plurality of portions selected on the basis of the data inputted to the selected portion input device is irradiated. That is, the radiation therapy planning apparatus according to the present invention can calculate the dose of the therapeutic radiation with which an arbitrary portion designated by a user is irradiated.

The three-dimensional data indicate positions of the affected part to be irradiated, the risky portion to be kept away from the irradiation, and a specific portion which can be measured by the marker position measurement part, in the subject. The specific portion measured by the marker position measurement part is a construction element of the subject itself, a marker provided on a body surface of the subject, or a marker provided inside a body of the subject, which can be measured by the marker position measurement part.

It is preferable in terms of reduction in the processing amount that the calculation method implemented in the position calculation part is based on a linear scaling in which such an estimation is carried out that distances from a fixed portion provided for the subject to the plurality of portions are extended or shortened in accordance with an extending or shortening change of a distance from the fixed portion to the specific portion.

It is preferable in terms of reduction in the error that the calculation method implemented in the position calculation part is based on a simulation method which estimates the positions of the plurality of portions by applying a simulation of a human body model in which a fixed portion provided for the subject and the position of the specific portion are preliminarily configured.

A radiation therapy planning method according to the present invention is provided with: collecting three-dimensional data representing a plurality of positions where a plurality of portions of a subject are positioned in a stationary state or a state at a specific timing; sequentially measuring a specific position of a specific portion out of the plurality of portions which changes in synchronization with a periodic movement of the subject; calculating time-dependent specific positions of the plurality of portions based on the three-dimensional data and the time-dependent specific position measured by the marker position measurement part; and calculating a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions.

The radiation therapy planning method according to one aspect of the present invention further includes: collecting from an irradiation recipe input device an irradiation recipe for irradiating the therapeutic radiation controlled so as to change based on the periodic motion of the subject; and calculating a dose of the therapeutic radiation in a case of being controlled in accordance with the irradiation recipe.

The radiation therapy planning method according to the present invention further includes: detecting a plurality of times corresponding to a plurality of phases of the periodic motion of the subject. The position of the specific portion indicates the position at the plurality of times.

The radiation therapy planning method according to the present invention further includes: calculating a dose of radiation with which the selected portion of the plurality of portions selected based on data inputted to a selected portion input device is irradiated.

The three-dimensional data indicate positions of an affected part to be irradiated, a risky portion to be kept away from the irradiation, and a specific portion which can be measured by the marker position measurement part, in the subject.

The specific portion is a construction element of the subject itself, a marker provided on a body surface of the subject, or a marker provided inside a body of the subject.

The positions of the plurality of portions are calculated by a linear scaling in which such an estimation is carried out that distances from a fixed portion provided for the subject to the plurality of portions are extended or shortened in accordance with an extending or shortening change of a distance from the fixed portion to the specific portion.

The positions of the plurality of portions are calculated by a simulation method which estimates the positions of the plurality of portions by applying a simulation of a human body model in which a fixed portion provided for the subject and the position of the specific portion are preliminarily configured.

A radiation therapy apparatus control device is provided with: a three-dimensional data collection part collecting three-dimensional data representing a plurality of positions where a plurality of portions of a subject are positioned; a marker position measurement part measuring a specific position of a specific portion of a plurality of portions; a position calculation part calculating an irradiation position of an irradiation portion of the plurality of portions based on the three-dimensional data and the specific position; and an irradiation control part moving a therapeutic radiation irradiation device by using a drive device so that the irradiation position is irradiated with therapeutic radiation. In the radiation therapy for treating an affected part changing in synchronization with the motion of the subject, it is required to sequentially specify positions of the respective portions of the subject, and to sequentially specify the position of the affected part in temporal sequence. The radiation therapy apparatus control device according to the invention reduces the dose of radiation with which the subject is irradiated in the case of calculating the time-dependent positions of the plurality of portions of the subject in comparison with a case of calculating the time-dependent positions of the subject on the basis of data measured by the 4D-CT.

It is preferable in terms of reduction of the processing amount that the position calculation part calculates the irradiation position by using a linear scaling for carrying out such estimation that a distance from a substantially fixed portion out of the plurality of portions to each of the plurality of portions is extended or shortened in accordance with an extending or shortening change of a distance from the fixed portion to the specific portion.

The radiation therapy apparatus control device according to the present invention further includes: a marker motion measurement part measuring a motion of the specific portion to generate motion data indicating the motion; and an affected part position table creation part creating an affected part position table that correlate a set of specific position motions with a set of positions, based on the three-dimensional data and the motion data. In this case, it is preferable in terms of reduction of the processing amount that the position calculation part refers to the affected part position table to calculate the irradiation position corresponding to the specific position out of the set of positions.

The radiation therapy apparatus control device according to the present invention further includes a phase detection part for detecting a plurality of times corresponding to a plurality of phases of a periodic motion of the subject. On this occasion, it is preferable that the set of positions in the affected part position table indicate positions of the specific portion at the plurality of times.

DETAILED DESCRIPTION OF THE INVENTION

Figure 1:
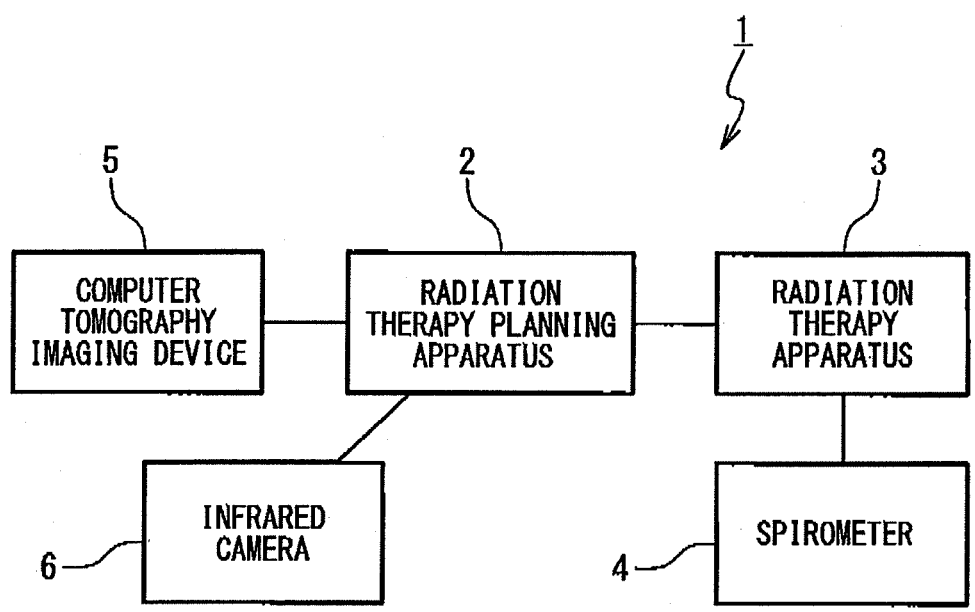
FIG. 1 is a block diagram showing an embodiment of a radiation therapy system.

Referring to drawings, embodiments of a radiation therapy system according to the present invention will be described. As shown in FIG. 1, the radiation therapy system 1 includes a radiation therapy planning apparatus 2, a radiation therapy apparatus 3, a spirometer 4, a computer tomography imaging device 5, and an infrared camera 6. The radiation therapy planning apparatus 2 is a computer such as a personal computer. The radiation therapy planning apparatus 2 is connected to the radiation therapy apparatus 3 so as to bi-directionally transmit data, and is connected to the spirometer 4, the computer tomography imaging device 5 and the infrared camera 6.

The spirometer 4 measures the ventilation volume when the patient breathes, and outputs the ventilation volume to the radiation therapy planning apparatus 2. The computer tomography imaging device 5 obtains a plurality of transmission images by transmitting X-rays through a human body in various directions, produces cross-section images of the human body through the image processing of the plurality of transmission images by a computer, and generates three-dimensional data representing the inner state of the human body through the image processing of the plurality of transmission images by the computer. The three-dimensional data represents the absorption degrees of the X-rays in respective portions within the human body. The infrared camera 6 images an infrared image of the patient by using reflected light of the infrared ray with which the patient is irradiated, and outputs the infrared image to the radiation therapy planning apparatus 2.

Figure 2:
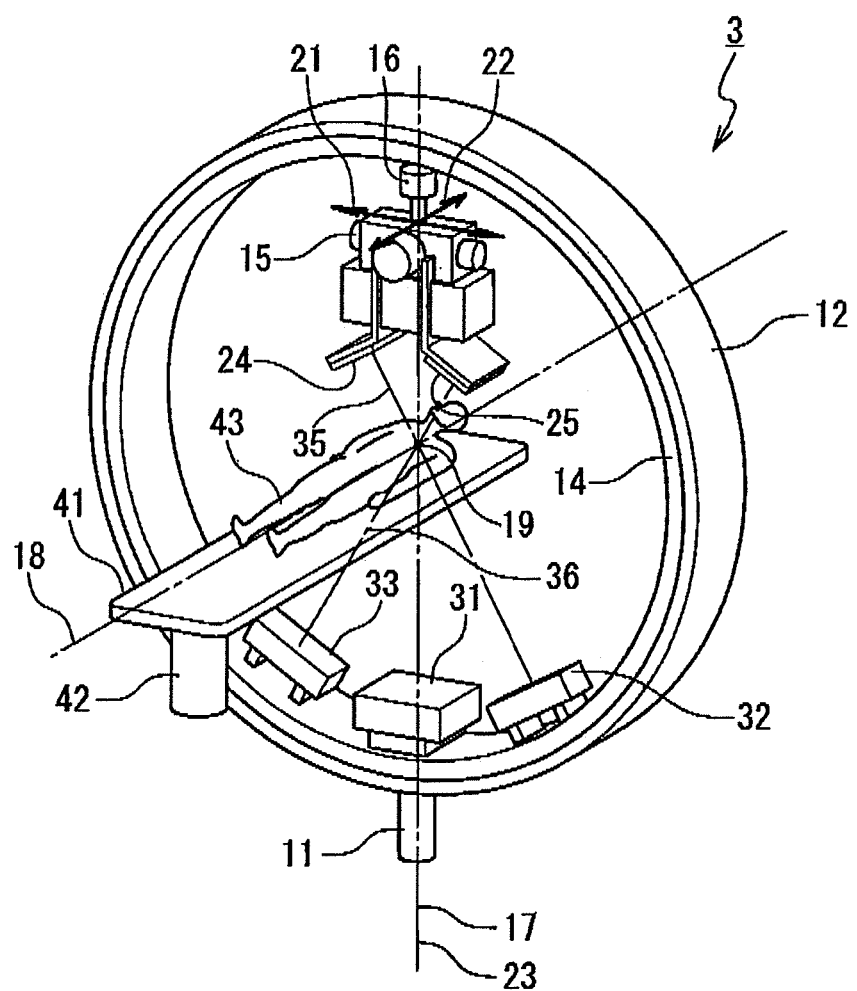
FIG. 2 is a perspective view showing a radiation therapy apparatus.

FIG. 2 shows the radiation therapy apparatus 3. The radiation therapy apparatus 3 includes a rotation drive device 11, an O-ring 12, a traveling gantry 14, an oscillation mechanism 15, and a therapeutic radiation irradiation device 16. The rotation drive device 11 supports the O-ring 12 on a base so as to be rotatable around a rotation axis 17, and rotates the O-ring 12 around the rotation axis 17 under a control of a radiation therapy apparatus control device not shown in the drawing. The rotation axis 17 is parallel to the vertical direction. The O-ring 12 is formed into a ring-shape centering around a rotation axis 18, and rotatably supports the traveling gantry 14 around the rotation axis 18. The rotation axis 18 is perpendicular to the vertical direction, and passes through an isocenter 19 included in the rotation axis 17. Moreover, the rotation axis 18 is fixedly defined with respect to the O-ring 12, and accordingly rotates around the rotation axis 17 together with the O-ring 12. The traveling gantry 14 is formed into a ring-shape centering around the rotation axis 18, and is arranged so as to be concentric with a ring of the O-ring 12. Furthermore, the radiation therapy apparatus 3 includes a traveling drive device not shown in the drawing. The traveling drive device rotates the traveling gantry 14 around the rotation axis 18 under the control of the radiation therapy apparatus control device.

The oscillation mechanism 15 is fixed inside a ring of the traveling gantry 14, and supports the therapeutic radiation irradiation device 16 on the traveling gantry 14 so that the therapeutic radiation irradiation device 16 can be arranged inside the traveling gantry 14. The oscillation mechanism 15 has a pan axis 21 and a tilt axis 22. The tilt axis 22 is fixedly defined with respect to the traveling gantry 14, and is parallel to the rotation axis 18 without intersecting the rotation axis 18. The pan axis 21 is orthogonal to the tilt angle 22. Under the control of the radiation therapy apparatus control device, the oscillation mechanism 15 rotates the therapeutic radiation irradiation device 16 around the pan axis 21 and rotates the therapeutic radiation irradiation device 16 around the tilt axis 22.

The therapeutic radiation irradiation device 16 emits therapeutic radiation 23 under the control of the radiation therapy apparatus control device. The therapeutic radiation 23 is emitted almost along a straight line passing the intersection where the pan axis 21 and the tilt axis 22 intersect each other. The therapeutic radiation 23 is formed so as to have an even intensity distribution. The therapeutic radiation irradiation device 16 has a MLC (Multi Leaf Collimator) not shown in the drawing, and further a part of the therapeutic radiation 23 is shielded by the MLC and thereby the shape of the irradiation field in irradiation of the therapeutic radiation 23 on the patient is controlled by the radiation therapy apparatus control device.

The therapeutic radiation irradiation device 16 is supported on the traveling gantry 14 in this manner, and accordingly, if once the therapeutic radiation irradiation device 16 is adjusted by the oscillation mechanism 15 to face the isocenter 19, the therapeutic radiation 23 generally passes the isocenter 19 constantly even when the O-ring 12 is rotated by the rotation drive device 11 or the traveling gantry 14 is rotated by the traveling drive device. That is, when the traveling and rotation are carried out, the therapeutic radiation 23 can be emitted from an arbitrary direction toward the isocenter 19.

The radiation therapy apparatus 3 further includes a plurality of imager systems. Specifically, the radiation therapy apparatus 3 includes diagnostic X-ray sources 24 and 25 and sensor arrays 32 and 33. The diagnostic X-ray source 24 is supported on the traveling gantry 14. The diagnostic X-ray source 24 is arranged inside the ring of the traveling gantry 14, and is arranged at a position where the angle between a line segment connecting the isocenter 19 to the diagnostic X-ray source 24 and a line segment connecting the isocenter 19 to the therapeutic radiation irradiation device 16 is acute. The diagnostic X-ray source 24 emits a diagnostic X-ray 35 toward the isocenter 19 under the control of the radiation therapy apparatus control device. The diagnostic X-ray 35 is emitted from one point of the diagnostic X-ray source 24, and is a conically-shaped cone beam having the one point as an apex. The diagnostic X-ray source 25 is supported on the traveling gantry 14. The diagnostic X-ray source 25 is arranged inside the ring of the traveling gantry 14, and is arranged at a position where the angle between a line segment connecting the isocenter 19 to the diagnostic X-ray source 25 and a line segment connecting the isocenter 19 to the therapeutic radiation irradiation device 16 is acute. The diagnostic X-ray source 25 emits a diagnostic X-ray 36 towards the isocenter 19 under the control of the radiation therapy apparatus control device. The diagnostic X-ray 36 is emitted from one point of the diagnostic X-ray source 25, and is a conically-shaped cone beam having the one point as an apex.

The sensor array 32 is supported on the traveling gantry 14. The sensor array 32 receives the diagnostic X-ray 35 which is emitted from the diagnostic X-ray source 24 and transmitted through the subject surrounding the isocenter 19, and generates a transmission image of the subject. The sensor array 33 is supported on the traveling gantry 14. The sensor array 33 receives the diagnostic X-ray 36 that is emitted from the diagnostic X-ray source 25 and transmitted through the subject surrounding the isocenter 19, and generates a transmission image of the subject. Examples of the sensor arrays 32 and 33 include an FPD (Flat Panel Detector) and an X-ray II (Image Intensifier).

This imager system allows generating a transmission image including the isocenter 19 at the center on the basis of image signals obtained from the sensor arrays 32 and 33.

The radiation therapy apparatus 3 further includes a sensor array 31. The sensor array 31 is arranged so that a line segment connecting the sensor array 31 to the therapeutic radiation irradiation device 16 passes the isocenter 19, and is fixed inside the ring of the traveling gantry 14. The sensor array 31 receives the therapeutic radiation 23 which is emitted from the therapeutic radiation irradiation device 16 and transmitted through the subject surrounding the isocenter 19, and generates a transmission image of the subject. Examples of the sensor array 31 include an FPD and an X-ray II.

The radiation therapy apparatus 3 further includes a couch 41 and a couch drive device 42. The couch 41 is used for a patient 43 to lie thereon, who is to be treated by the radiation therapy system 1. The couch 41 includes a fixture not shown in the drawing. The fixture fixes the patient on the couch 41 so that the patient does not move. The couch drive device 42 supports the couch 41 on the base, and moves the couch 41 under the control of the radiation therapy apparatus control device.

Figure 3:
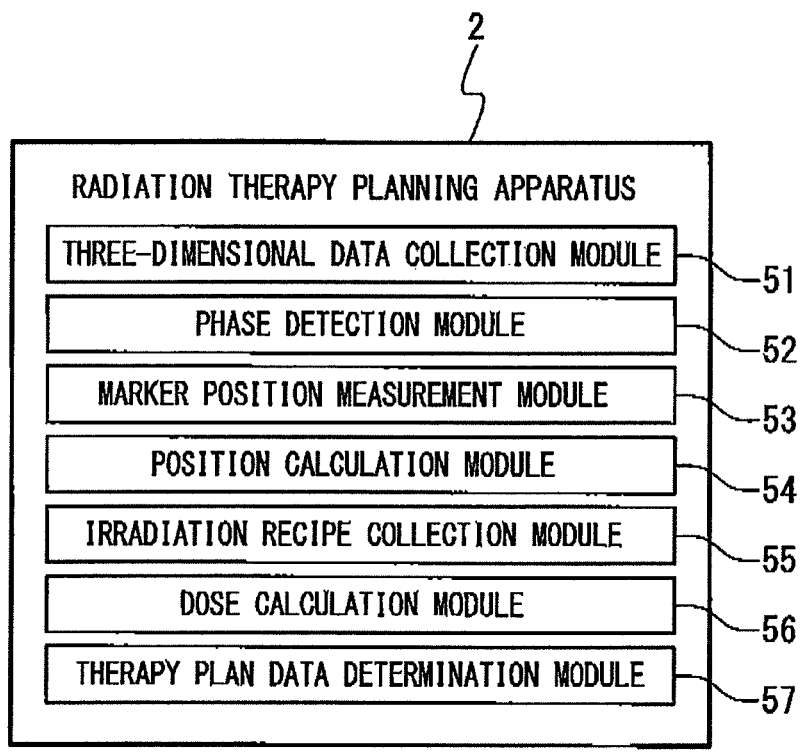
FIG. 3 is a block diagram showing an embodiment of a radiation therapy planning apparatus according to the present invention.

FIG. 3 shows the radiation therapy planning apparatus 2. The radiation therapy planning apparatus 2 is a computer, and includes an CPU, a storage device, an input device, an output device, and an interface that are not shown in the drawing. The CPU executes a plurality of computer programs installed onto the radiation therapy planning apparatus 2 to control the storage device, the input device, the output device, and the interface. The storage device records the computer programs, data used by the CPU, and data generated by the CPU. The input device outputs data generated by a user's operation to the CPU. The output device outputs data generated by the CPU so that the user can recognize the data. As the input device, a keyboard and a mouse are exemplified. As the output device, a display for displaying an image generated by the CPU is exemplified. Moreover, as the input device or the output device, a removable memory drive and a communication device are exemplified. The removable memory drive outputs data recorded in a removable memory to the CPU, and records data generated by the CPU to the removable memory. As the removable memory, a flash memory, a magnetic disk (a flexible disk and a hard disk), a magnetic tape (a video tape), an optical disk (a CD and a DVD), and a magneto-optical disk are exemplified. The communication device sends data generated by the CPU to another, computer via a communication line network, and outputs data outputted from another computer to the CPU via the communication line network. As the communication line network, a LAN, the internet, and a dedicated line are exemplified. The interface outputs to the CPU data generated by an external device connected to the radiation therapy planning apparatus 2, and outputs data generated by the CPU to the external device. The external device includes the radiation therapy apparatus 3, the spirometer 4, and the computer tomography imaging device 5.

The computer programs include a three-dimensional data collection module 51, a phase detection module 52, a marker position measurement module 53, a position calculation module 54, an irradiation recipe collection module 55, a dose calculation module 56, and a therapy plan data determination module 57.

The three-dimensional data collection module 51 collects three-dimensional data of the patient 43 generated by the computer tomography imaging device 5 from the computer tomography imaging device 5, and records the three-dimensional data, with the three-dimensional data correlated with identification data of the patient 43. The three-dimensional data represent the transmission amounts of the X-rays in multiple portions of the patient 43.

The phase detection module 52 obtains from the spirometer 4 the ventilation volume of the case where the patient 43 breathes. The phase detection module 52 divides the breathing of the patient 43 into a plurality of steps (the breathing phases) on the basis of the ventilation volume measured by the spirometer 4, and detects respective times when the breathing reaches the respective steps on the basis of the ventilation volume measured by the spirometer 4.

The marker position measurement module 53 sequentially images transmission images of the patient 43, with the transmission images correlated with the imaging times, by using the imager system of the radiation therapy apparatus 3. The marker position measurement module 53 calculates motions (or movements) of markers (described in detail below) on the basis of the transmission images and the times detected by the phase detection module 52. The motions of the markers indicate the positions of the marker at the respective times detected by the phase detection module 52, and indicate the positions of the markers of each breathing phase. Furthermore, the marker position measurement module 53 may sequentially image the transmission images of the patient 43, with the transmission images correlated with the imaging times, by using the infrared camera 6, and additionally calculate of the motions of the markers based on the infrared images and the times detected by the phase detection module 52.

The position calculation module 54 calculates the motions (the movements) of the respective portions of the patient 43 on the basis of the three-dimensional data collected by the three-dimensional data collection module 51 and the motions of the markers calculated by the marker position measurement module 53. The motions of the portions indicate the positions of the portions at each breathing phase. Examples of this calculation method of the positions include a linear scaling and a simulation. The linear scaling is a method for estimating the positions of all the portions so that the distance from the fixed portion to each of the respective portions is linearly extended or shortened in accordance with changes in which the distances from a substantially-fixed portion out of the portions (a fixed portion contacting the couch or a substantially-fixed portion) to the markers are linearly extended or shortened. As the fixed portion, the pelvis and the backbone are exemplified. The simulation is a method for estimating the positions of all the portions by using a mathematical human body model on the basis of: the position of the fixed portion out of the respective portions; and the positions of the markers.

The irradiation recipe collection module 55 collects an irradiation recipe from the input device, when the irradiation recipe is inputted to the input device by the user. The irradiation recipe indicates reference irradiation angles, prescribed doses, and an irradiation method. The reference irradiation angles indicate the directions of the therapeutic radiation 23 with which the affected part of the patient 43 is irradiated, and indicate a traveling angle and a rotation angle. The traveling angle means the direction of the traveling gantry 14 rotated by the traveling drive device. The rotation angle means the direction of the O-ring 12 rotated by the rotation drive device 11. The prescribed doses indicate the doses of the therapeutic radiation 23 with which the affected part is irradiated from the respective reference irradiation angles.

As the irradiation method, the moving body tracking irradiation and the gated irradiation are exemplified. The moving body tracking irradiation is exemplified by position correction tracking irradiation, shape correction tracking irradiation (the MLC control), and combination of the position correction tracking irradiation and the shape correction tracking irradiation. The position correction tracking irradiation is a method for changing a relative position of the therapeutic radiation 23 to the patient 43 on the basis of a measured value measured by using the spirometer 4 (or the imager system). The shape correction tracking irradiation is a method for changing a shape of the irradiation field of the therapeutic radiation 23 on the basis of a measured value measured by using the spirometer 4 (or the imager system). The gated irradiation is a method for emitting the therapeutic radiation 23, in which the therapeutic radiation 23 is emitted or stopped on the basis of a measured value measured by using the spirometer 4 (or the imager system).

The irradiation recipe collection module 55 further calculates a detailed irradiation method on the basis of the inputted irradiation recipe. For example, when the position correction tracking irradiation is chosen as the irradiation method, the irradiation recipe collection module 55 calculates how the relative position of the therapeutic radiation 23 to the patient 43 changes with the breathing phase, that is, calculates how to rotate the therapeutic radiation irradiation device 16 around the pan axis 21 and the tilt axis 22 by using the oscillation mechanism 15. When the shape correction tracking irradiation is chosen as the irradiation method, the irradiation recipe collection module 55 calculates how the irradiation field of the therapeutic radiation 23 changes with the breathing phase, that is, calculates how to control the MLC of the therapeutic radiation irradiation device 16. When the gated irradiation is chosen as the irradiation method, the irradiation recipe collection module 55 calculates which timing of the breathing phase the irradiation is to be stopped and started.

On the basis of the motion calculated by the position calculation module 54, the dose calculation module 56 calculates the dose of the therapeutic radiation 23 with which each of a plurality of portions is irradiated for the case where the patient 43 is irradiated with the therapeutic radiation 23 in the irradiation method collected by the irradiation recipe collection module 55. The calculated dose indicates the accumulated dose which is defined as the sum of the radiation dose irradiated in each of minute periods defined by dividing the period during which the irradiation method is carried out.

Moreover, the dose calculation module 56 displays the three-dimensional data on a display so that the user can recognize the data, and calculates the position of the portion corresponding to the contour inputted by the user, out of the respective portions. Furthermore, when the patient 43 is irradiated with the therapeutic radiation 23 in the irradiation method collected by the irradiation recipe collection module 55, the dose calculation module 56 calculates the accumulated dose of the therapeutic radiation 23 with which the selected portion is irradiated, and calculates the DVH (Dose Volume Histograms) related to the selected portion. As the portion to be selected, an affected part of the patient 43 and a risky organ are exemplified.

The therapy plan data determination module 57 creates and determines a therapy plan, when the dose calculated by the dose calculation module 56 is appropriate. The therapy plan is comprised of a combination of: the irradiation method specified by the irradiation recipe collection module 55; and the detailed irradiation method calculated by the irradiation recipe collection module 55.

Figure 4:
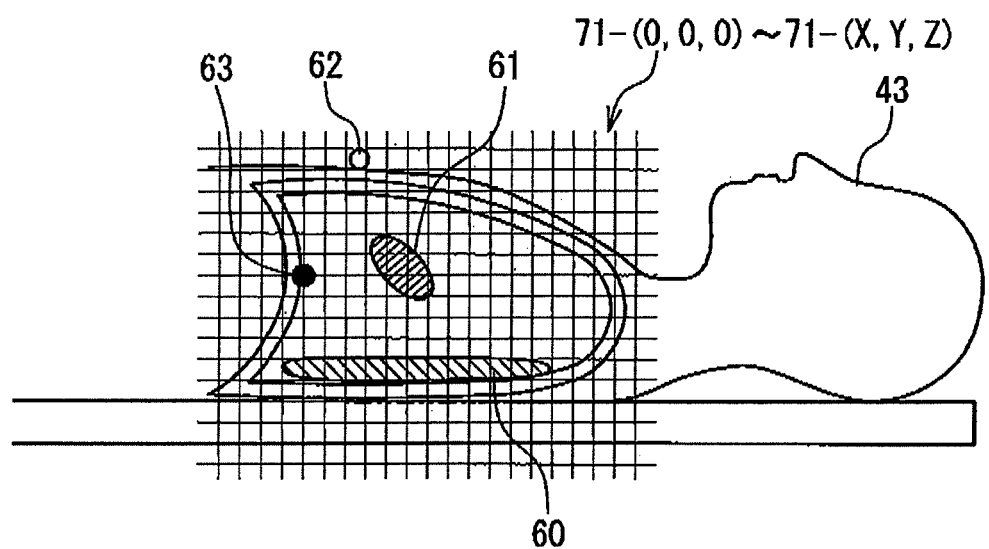
FIG. 4 is a diagram showing a patient.

FIG. 4 shows the three-dimensional data collected by the three-dimensional data collection module 51. The three-dimensional data sterically represent the subject to correlate a plurality of transmittances with a plurality of VOXELs 71-(0, 0,0) to 71-(X,Y,Z). The VOXELs 71-(0,0,0) to 71-(X,Y,Z) correspond to a plurality of cubes tightly filling the space where the subject (the patient 43) is arranged. As the length of one side of the cubes, 1 cm is exemplified. The transmittance corresponding to each VOXEL 71-$(x,y,z)$ (x=0,1,2, . . . , X, y=0,1,2, . . . , Y, and z=0, 1, 2, . . . , Z) of the VOXELS 71-(0,0,0) to 71-(X,Y,Z) indicate the transmittance of the X-ray of the cube arranged at the position (x,y,z) corresponding to one of the VOXELs 71-$(x,y,z)$ at a given time (at a certain breathing phase).

The three-dimensional data indicate the patient 43. The patient 43 has an affected part 61 and a risky organ 60. The affected part 61 implies a portion at which a disease exists, and a portion which should be irradiated with the therapeutic radiation 23. As the affected part 61, a part of the lung is exemplified. The risky organ 60 implies an organ other than the affected part 61, and is a portion which should not be irradiated with the therapeutic radiation 23. As the risky organ 60, the bone marrow is exemplified. Moreover, a body surface marker 62 and a gold marker 63 are arranged on the patient 43. The body surface marker 62 is imaged on an infrared image obtained by the infrared camera 6, and is adhered on the body surface of the patient 43. The gold marker 63 is a ball formed of gold, and is implanted in the body of the patient 43 so as to move in synchronization with the breathing of the patient 43.

Meanwhile, the gold marker 63 may be formed in a shape other than a ball. As the shape, a coiled shape is exemplified. The gold marker 63 may be formed of material other than gold. As the material, platinum is exemplified. The gold marker 63 may be replaced with a different landmark moving in synchronization with the breathing of the patient 43. The landmark is detected by the imager system, and the organ of the patient is exemplified as the landmark. As the organ, the bone (a rib), the diaphragm, and the affected part itself are exemplified. The gold marker 63 may be replaced by a different marker detected by a detector different from the imager system. As the marker, a capsule generating a radio wave is exemplified.

On this occasion, the marker position measurement module 53 calculates the motion of the gold marker 63 on the basis of: the transmission images of the patient 43 sequentially obtained by using the imager system of the radiation therapy apparatus 3; and the times detected by the phase detection module 52. The marker position measurement module 53 calculates the motion of the body surface marker 62 on the basis of: the infrared images of the patient 43 sequentially obtained by using the infrared camera 6; and the times detected by the phase detection module 52.

The position calculation module 54 calculates how the respective portions corresponding to the VOXELs 71-(0,0,0) to 71-(X,Y,Z) move on the basis of: the three-dimensional data, the motion of the body surface marker 62 calculated by the marker position measurement module 53; and the motion of the gold marker 63. Specifically, the position calculation module 54 creates plural pieces of three-dimensional data at each of the breathing phases detected by the phase detection module 52 on the basis of the three-dimensional data and the motion of the markers. In the similar manner of the three-dimensional data collected by the three-dimensional data collection module 51, the plural pieces of the three-dimensional data are composed of a plurality of VOXELs, and are calculated so that the positions corresponding to a certain VOXEL 71-($x,y,z$) of the three-dimensional data corresponding to different breathing phases are different. Meanwhile, regarding the calculation of the motions of the respective portions, the motions of both of the body surface marker 62 and the motion of the gold marker 63 are not necessarily needed, and also the position calculation module 54 may calculate the motions of the respective portions on the basis of either one of the motion of the body surface marker 62 and the motion of the gold marker 63.

Moreover, the number of the VOXELs corresponding to the affected part 61 out of the VOXELs 71-(0,0,0) to 71-(X, Y,Z) is plural. The number of the VOXELs corresponding to the risky organ 60 of the VOXELs 71-(0,0,0) to 71-(X,Y,Z) is plural. As described above, by designing sizes of the VOXELs 71-(0,0,0) to 71-(X,Y,Z), the position calculation module 54 can calculate the motion in each of a plurality of portions obtained by dividing the affected part 61 (or the risky organ 60), and as a result, the deformation of the affected part 61 (or the risky organ 60) can be calculated. By thus designing the sizes of the VOXELs 71-(0,0,0) to 71-(X,Y,Z), the dose calculation module 56 further can calculate the dose irradiated on each of the portions obtained by dividing the affected part 61 (or the risky organ 60).

Figure 5:
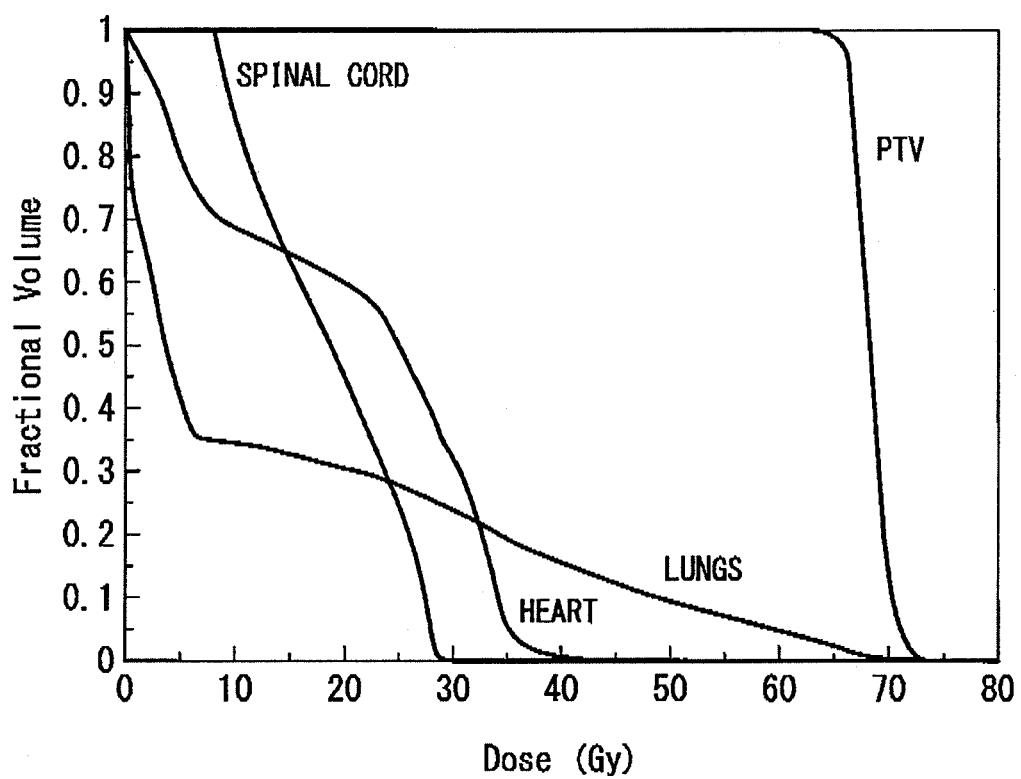
FIG. 5 is a graph showing a DVH (Dose Volume Histograms)

FIG. 5 shows the DHV calculated by the dose calculation module 56. The DHV indicates the ratio of the portions which are irradiated with a dose more than a certain level with respect to a portion selected by the user's operation. As this portion, the heart, the lung, the spinal cord, and the PTV (Planning Target Volume) are exemplified. The PTV indicates a region including an internal target volume and a Set-up Margin (SM). The Set-up Margin indicates a region around the internal target volume, and indicates a region in every irradiation. The internal target volume indicates a region including a clinical target volume and an internal margin (IM). The internal margin means a region around the clinical target volume, and means a region where the clinical target volume moves due to the motion of the internal organ such as the breathing, the swallowing, the cardiac motion, the peristalsis, and expansion of the bladder. The clinical target volume indicates a region including a gross tumor volume and a minute portion. The minute portion means a microscopic extensive range around the gross tumor volume and a minute portion, or means a region including a lymph node to which the tumor belongs. The gross tumor volume indicates a region judged to have a tumor by the diagnostic imaging, the palpation, and the inspection. According to the above-described DIV, the user, especially a medical doctor can easily judge whether or not the therapeutic radiation 23 is appropriately emitted.

Figure 6:
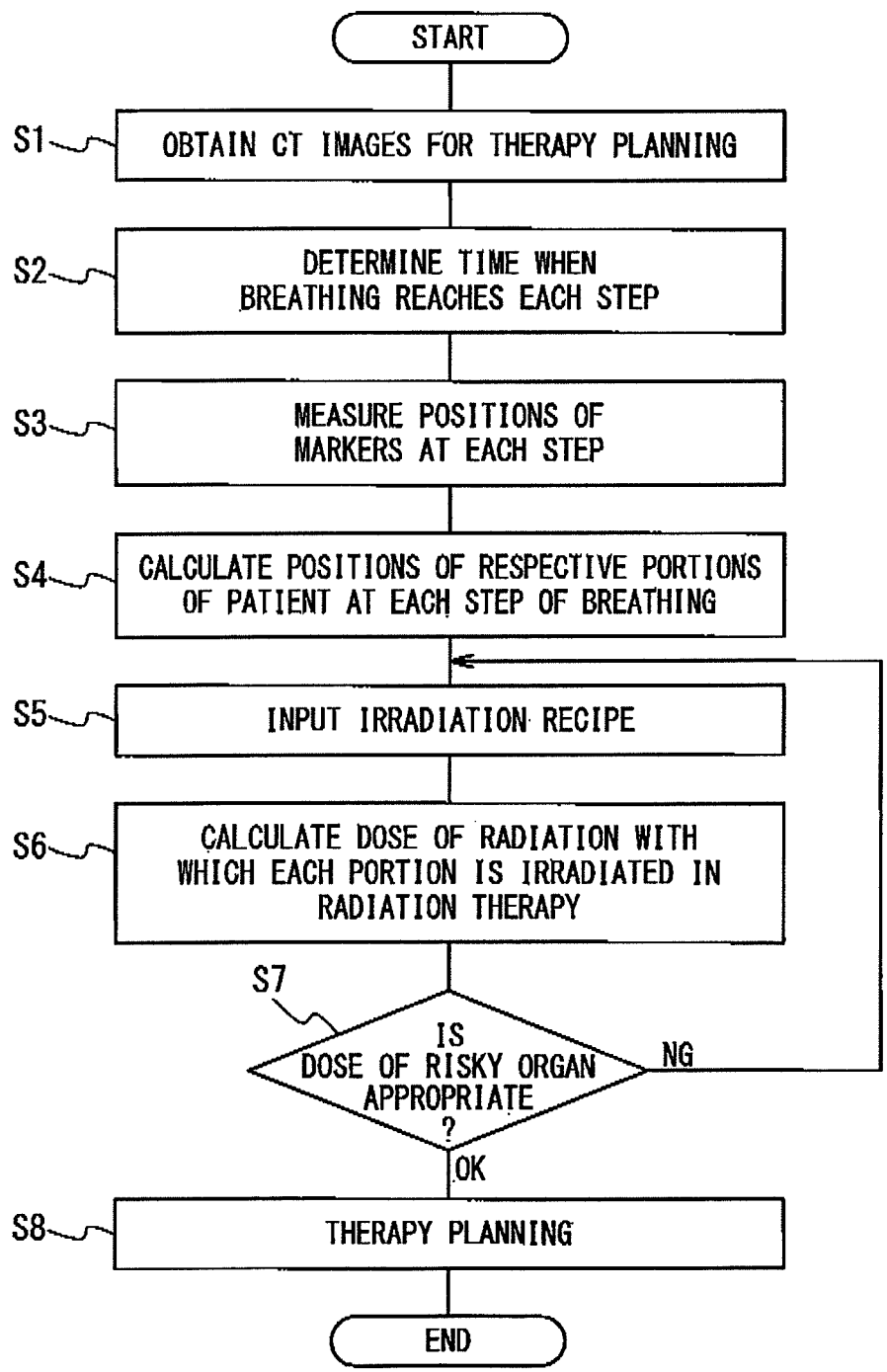
FIG. 6 is a flowchart showing an embodiment of a radiation therapy planning method according to the present invention.

FIG. 6 shows an embodiment of the radiation therapy planning method according to the present invention. At first, the user creates three-dimensional data of the affected part of the patient 43; and a portion around the affected part by using the computer tomography imaging device 5 (Step S1). The radiation therapy planning apparatus 2 generates an image showing the affected part of the patient 43 and the organ around the affected part on the basis of the three-dimensional data generated by the computer tomography imaging device 5, and shows the image on the display. The user views the image by using the radiation therapy planning apparatus 2, inputs data indicating the contour of a region in which the affected part 61 is shown in the image to the radiation therapy planning apparatus 2, and inputs data indicating the contour of a region in which the risky organ 60 is shown in the image to the radiation therapy planning apparatus 2. The radiation therapy planning apparatus 2 calculates the position of the patient 61 and the position of the risky organ 60 on the basis of the data.

Moreover, the user fixes the patient 43 on the couch 41 of the radiation therapy apparatus 3 so that the patient 43 can take the same stance as that of the case where the three-dimensional data has been obtained by using the computer tomography imaging device 5, and sets the spirometer 4 to observe the breathing of the patient 43. The radiation therapy planning apparatus 2 collects the ventilation volume from the spirometer 4, and on the basis of the ventilation volume, detects the times at which the breathing reaches the respective steps (Step S2). The radiation therapy planning apparatus 2 obtains infrared images of the patient 43 by using the infrared camera 6, detecting the breathing phases by using the spirometer 4. The radiation therapy planning apparatus 2 irradiates the patient 43 with the diagnostic X-ray 35 by using the diagnostic X-ray source 24, detecting the breathing phase by using the spirometer 4, and obtains the transmission images of the affected part of the patient 43 by using the sensor array 32. Moreover, the radiation therapy planning apparatus 2 emits the diagnostic X-ray 36 by using the diagnostic X-ray source 25, detecting the breathing phase by using the spirometer 4, and images the transmission images of the affected part of the patient 43 by using the sensor array 33.

Based on the infrared images, the radiation therapy planning apparatus 2 calculates how the body surface marker 62 moves in accordance with the breathing. That is, based on the infrared images, the radiation therapy planning apparatus 2 calculates the positions of the body surface marker 62 at the times at which the breathing reaches the respective steps.

Moreover, based on the transmission images, the radiation therapy planning apparatus 2 calculates how the gold marker 63 moves in accordance with the breathing. That is, based on the transmission images, the radiation therapy planning apparatus 2 calculates the positions of the gold marker 63 at the times at which the breathing reaches the respective steps (Step S3).

Based on the motion of the body surface marker 62 and the motion of the gold marker 63, the radiation therapy planning apparatus 2 calculates the motions of the portions of the patient 43 corresponding to the VOXELs 71-(0,0,0) to 71-(X, Y,Z), and calculates the positions of the portions of the patient 43 at each breathing phase (step S4).

Next, the user inputs an irradiation recipe expected to be appropriate to the radiation therapy to the radiation therapy planning apparatus 2 (step S5). The irradiation recipe indicates the reference irradiation angles, the prescribed dose, and the irradiation method. The reference irradiation angle mean the direction in which the affected part of the patient 43 is irradiated with the therapeutic radiation 23. The prescribed dose means the dose of the therapeutic radiation 23 with which the affected part the irradiated from each reference irradiation angle. When the irradiation recipe indicates the position correction tracking irradiation, the radiation therapy planning apparatus 2 calculates how the relative position of the therapeutic radiation 23 with respect to the patient 43 changes with the breathing phase. When the irradiation recipe indicates the position correction tracking irradiation, the radiation therapy planning apparatus 2 calculates how the irradiation field of the therapeutic radiation 23 changes with the breathing phase, that is, calculates how the MLC of the therapeutic radiation irradiation device 16 should be controlled. When the irradiation recipe indicates the gated irradiation, the radiation therapy planning apparatus 2 calculates which timing of the breathing phase the irradiation is to be stopped and started.

Based on the calculated motions of the portions, the radiation therapy planning apparatus 2 calculates the doses of the therapeutic radiation 23 with which the portions are irradiated, when the patient 43 is irradiated with the therapeutic radiation 23 in accordance with the irradiation recipe. Moreover, based on the contour inputted by the user, the radiation therapy planning apparatus 2 specifies the position of the affected part 61, calculates the dose of the therapeutic radiation 23 with which the affected part 61 is irradiated, and calculates the DHV of the affected part 61. Furthermore, the radiation therapy planning apparatus 2 specifies the position of the risky organ 60 on the basis of the contour inputted by the user, calculates the dose of the therapeutic radiation 23 with which the risky organ 60 is irradiated, and calculates the DVH of the risky organ 60 (step S6).

Based on the DVH of the affected part 61 and the DVH of the risky organ 60, the user judges whether the irradiation recipe is appropriate or inappropriate (Step S7). When the irradiation recipe is inappropriate (Step S7, NG), the user inputs an irradiation recipe expected to be appropriate to the radiation therapy to the radiation therapy planning apparatus 2 again (Step S5). When the irradiation recipe is appropriate (Step S7, OK), the user creates the therapeutic plan so that the irradiation recipe is included, and determine the therapeutic plan (Step S8).

In the same manner as that of the commonly-known radiation therapy, the radiation therapy based on the therapy plan created in this manner is carried out by the radiation therapy apparatus 3. That is, when the position correction tracking irradiation is selected by the user, the radiation therapy apparatus 3 calculates the position of the affected part on the basis of the amount collected from the spirometer 4 or the amount measured by using the imager system, and moves the therapeutic radiation irradiation device 16 by using the oscillation mechanism 15 so that the therapeutic radiation 23 pass through the position of the affected part. When the shape correction tracking irradiation is selected by the user, the radiation therapy apparatus 3 changes the shape of the irradiation field of the therapeutic radiation 23 on the basis of the amount collected from the spirometer 4 or the amount measured by using the imager system. When the gated irradiation is selected by the user, the radiation therapy apparatus 3 irradiates and stops the therapeutic radiation 23 on the basis of the amount collected from the spirometer 4 or the amount measured by using the imager system.

According to this radiation therapy planning method, the creation of the therapy plan only requires generation of one piece of the three-dimensional data by using the computer tomography imaging device 5, and the dose of radiation with which the patient 43 is irradiated is reduced in the case of calculating the motions of the portions corresponding to the VOXELs of the patient 43 in comparison with a case of calculating the motions the portions corresponding to the VOXELs of the patient 43 on the basis of information measured by the 4D-CT. Moreover, according to this radiation therapy planning method, in the same manner as that of calculating the dose by using the motions of the portions calculated by using the 4D-CT, the dose of the therapeutic radiation 23 with which the respective portions of the patient 43 irradiated in the radiation therapy can be calculated accurately.

Generally, the three-dimensional data detected by the 4D-CT has a rough time resolution, and it is difficult to make the time resolution more accurate than the breathing phases divided by using the spirometer 4. Furthermore, according to this radiation therapy planning method, the time resolution to detect the motions of the markers can be improved more easily in comparison with the 4D-CT, and on this occasion, the dose of the therapeutic radiation 23 with which the respective portions of the patient 43 are irradiated in the radiation therapy can be calculated more accurately.

When the doses of radiations with which the affected part 61 and the risky organ 60 are irradiated are calculated on the basis of data measured by the 4D-CT, the user is required to input the contours of the affected part 61 or the risky organ 60 regarding each of pieces of the three-dimensional data detected at each of the times to the radiation therapy planning apparatus. According to the radiation therapy planning method of the present invention, when the accumulated dose with which the affected part 61 or the risky organ 60 is irradiated is calculated, the user is only required to input the contour of the affected part 61 or the risky organ 60 regarding the three-dimensional data corresponding to one breathing phase to the radiation therapy planning apparatus; the effort of the user can be reduced in comparison with the calculation of the accumulated dose based on the information measured by the 4D-CT, and accordingly the therapy plan can be created more rapidly.

It should be noted that the spirometer 4 may be replaced with another spirograph which measures a physical quantity other than the ventilation volume. As the spirograph, a camera is exemplified. The camera images the surface of the thorax of the patient, and measures the position of the surface. Moreover, the spirometer 4 may be replaced with a motion detection device which monitors another motion other than the breathing of the human body. As the motion, a periodic motion and a non-periodic motion are exemplified. As the periodic motion, the heartbeat is exemplified. As the motion detection device for detecting the heartbeat, an electrocardiograph, a pulse monitor, and a sphygmomanometer are exemplified. The electrocardiograph is a device which creates an electrocardiogram of the patient, and measures the active volume of the heart of the patient. The pulse monitor measures the pulse of the patient. As the non-periodic motion, the swallowing and the expansion of the bladder are exemplified.

It should be noted that the imager system of the radiation therapy apparatus 3 may be replaced with another device which measures the position of the gold marker 63 (or the landmark moving linked to the breathing). As the device, an MRI apparatus, a PET (Positron Emission Tomography) inspection apparatus, an SPECT (Single Photon Emission Computed Tomography), and an ultrasonic inspection apparatus are exemplified. The MRI apparatus detects magnetism included in cells of a human body by using the nuclear magnetic resonance, images the magnetism by using a computer, and generates three-dimensional data representing the inner state of the human body. The PET inspection apparatus generates the three-dimensional data representing the inner state of the human body by using a compound labeled by a nuclide of positron decay as a radioactive tracer. The SPECT detects a distribution of γ-ray emitted from a radio isotope given in the body, and generates the three-dimensional data representing the inner state of the human body on the basis of the distribution. The ultrasonic inspection apparatus generates ultrasonic toward the human body, and generates the three-dimensional data representing the inner state of the human body on the basis of the reflected ultrasonic (echo).

Meanwhile, the infrared camera 6 may be replaced with another device which measures the position of the body surface marker 62. As the device, a CCD camera and a laser gauge are exemplified. The CCD camera takes an image of the patient by using reflected light of visible light with which the patient is irradiated, and outputs the image to the radiation therapy planning apparatus 2. The laser gauge scans an infrared laser over a region where the body surface marker 62 is arranged, and measures the position of the body surface marker 62 on the basis of: reciprocation time of the infrared laser between the body surface marker 62 and the sensor; and a direction in which the infrared laser has been emitted.

It should be noted that the phase detection module 52 may calculate the position of the body surface marker 62 on the basis of the infrared image taken by the infrared camera 6, and detect the time at which the breathing of the patient 43 reaches each step on the basis of the position. Moreover, the phase detection module 52 may calculate the position of the gold marker 63 on the basis of the transmission image imaged by the imager system of the radiation therapy apparatus 3, and detect the time at which the breathing of the patient 43 reaches each step on the basis of the position. On this occasion, the radiation therapy system 1 does not require the spirometer 4, which is preferable.

It should be noted that the radiation therapy planning method according to the present invention may be applied to another radiation therapy apparatus other than the radiation therapy apparatus 3. This radiation therapy apparatus includes a commonly-known radiation therapy apparatus which can carry out the moving body tracking irradiation or the gated irradiation. As the commonly-known radiation therapy apparatus, a device for supporting the therapeutic radiation irradiation device 16 with a robot arm and a radiation therapy apparatus whose member for supporting the therapeutic radiation irradiation device 16 is formed in a shape other than the O-ring shape are exemplified. As the shape, a C-shape, an O-shape, and an L-shape are exemplified.

Figure 7:
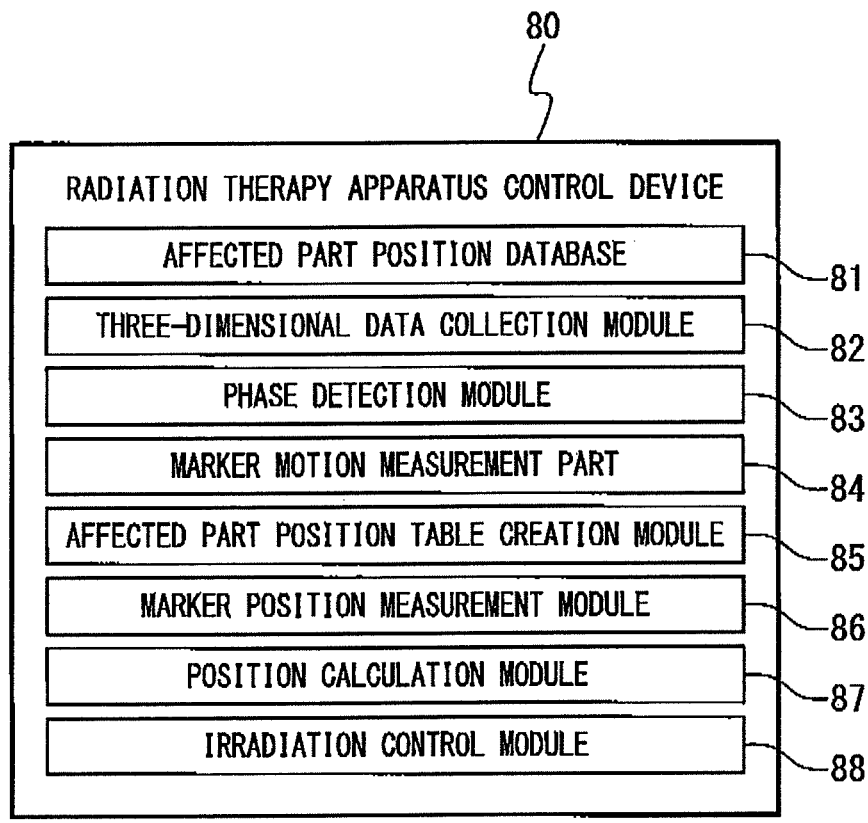
FIG. 7 is a block diagram showing an embodiment of a radiation therapy apparatus control device according to the present invention.

FIG. 7 shows an embodiment of the radiation therapy apparatus control device according to the present invention. The radiation therapy apparatus control device 80 is a computer, and has a CPU not shown in the drawing, a storage device, an input device, an output device, and an interface. The CPU executes computer programs installed onto the radiation therapy apparatus control device 80 to control the storage device, the input device, and the output device. The storage device records the computer programs, records data used by the CPU, and records data generated by the CPU. The input device outputs data generated by the user's operation to the CPU. As the input device, a keyboard and a mouse are exemplified. The output device outputs data generated by the CPU to the used in a visible manner. As the output device, a display is exemplified. The interface outputs data generated by external apparatuses connected to the radiation therapy apparatus control device 80 to the CPU, and outputs data generated by the CPU to the external apparatuses. The external apparatuses include the spirometer 4, the computer tomography imaging device 5, the infrared camera 6, the rotation drive device 11 of the radiation therapy apparatus 3, the travel drive device, the oscillation mechanism 15, the therapeutic radiation irradiation device 16, the MLC, the imager system (the diagnostic X-ray sources 24 and 25, and the sensor arrays 31, 32, and 33), and the couch drive device 42.

The computer programs include an affected part position database 81, a three-dimensional data collection module 82, a phase detection module 83, a marker motion measurement module 84, an affected part position table creation module 85, a marker position measurement module 86, a position calculation module 87, and an irradiation control module 88.

The affected part position database 81 records an affected part position table indicating an association of the positions of the markers and the position of the affected part in the storage device so that the table is searchable and changeable by another computer program.

In the same manner as that of the three-dimensional data collection module 51, the three-dimensional data collection module 82 collects the three-dimensional data of the patient 43 generated by the computer tomography imaging device 5 from the computer tomography imaging device 5, and records the three-dimensional data to the storage device. The three-dimensional data shows degrees of the transmission amounts of the X-ray in the plurality of portions of the patient 43.

In the same manner as that of the phase detection module 52, the phase detection module 83 collects the ventilation volume of the breathing of the patient 43 from the spirometer 4. The phase detection module 83 divides the breathing of the patient 43 into a plurality of steps (the breathing phases) on the basis of the ventilation volume measured by the spirometer 4, and detects the times when the breathing reaches the respective steps on the basis of the ventilation volume measured by the spirometer 4.

In the same manner as that of the marker position measurement module 53, the marker motion measurement module 84 sequentially images transmission images by using the imager system of the radiation therapy apparatus 3, with the transmission images of the patient 43 correlated with the imaging times. The marker motion measurement module 84 calculates the movement (the motion) of the gold marker 63 on the basis of the transmission images and the times detected by the phase detection module 83. Moreover, the marker motion measurement module 84 sequentially images the infrared images by using the infrared camera 6 with the infrared images of the patient 43 correlated with the imaging times, and calculates the movement of the body surface marker 62 on the basis of the infrared images and the times detected by the phase detection module 52. Such movements of the markers indicate the positions of the markers at the times detected by the phase detection module 83, and indicate the positions of the markers at each breathing phase.

On the basis of the positions of the markers at each breathing phase calculated by the marker motion measurement module 84 and the three-dimensional data collected by the three-dimensional data collection module 82, the affected part position table creation module 85 calculates the movements (the motions) of the respective portions of the patient 43. The movements of the portions indicate the positions of the portions at each breathing phase. As this calculation method of the positions, the linear scaling and the simulation are exemplified. On the basis of the movements of the respective portions and the positions of the markers at each breathing phase calculated by the marker motion measurement module 84, the affected part position table creation module 85 calculates the movement of the affected part, and creates the affected part position table recorded in the affected part position database 81.

The marker position measurement module 86 obtains the transmission images of the patient 43 by using the imager system of the radiation therapy apparatus 3. The marker position measurement module 86 calculates the position of the gold marker 63 on the basis of the transmission images. Moreover, the marker position measurement module 86 sequentially obtains the infrared images by using the infrared camera 6 with the infrared images of the patient 43 correlated to the imaging times, and calculates the position of the body surface marker 62 on the basis of the infrared images.

Referring to the affected part position table recorded by the affected part position database 81, the position calculation module 87 calculates the affected part position, which is related to the positions of the markers collected by the marker position measurement module 86.

The irradiation control module 88 drives the therapeutic radiation irradiation device 16 by using the oscillation mechanism 15 so that the therapeutic radiation 23 transmits through the affected part position calculated by the position calculation module 87, and controls the shape of the irradiation field of the therapeutic radiation 23 by using the MLC. Furthermore, after the driving of the therapeutic radiation irradiation device 16, the irradiation control module 88 irradiates the affected part position with the therapeutic radiation 23 by using the therapeutic radiation irradiation device 16. It should be noted that the irradiation control module 88 may change the positional relationship between the patient 43 and the therapeutic radiation irradiation device 16 so that the therapeutic radiation 23 can transmit through the affected part position by further using the rotation drive device 11, the travel drive device, or the couch drive device 42.

Figure 8:
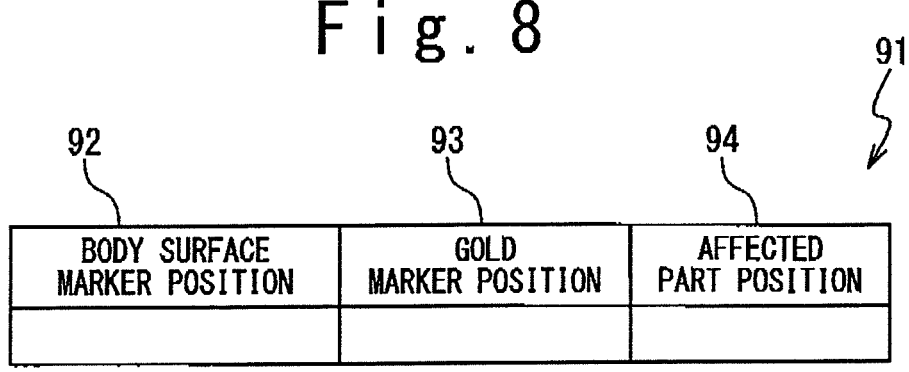
FIG. 8 is a diagram showing a patient position table.

FIG. 8 shows the affected part position table recorded in the storage device by the affected part position database 81. The affected part position table 91 correlates a set of body surface marker Positions 92 and a set of gold marker positions 93 with a set of affected part positions 94. That is, a combination of an arbitrary element of the body surface marker position aggregation 92 and an arbitrary element of the gold marker position aggregation 93 corresponds to one element of the affected part position aggregation 94. The elements of the set of the body surface marker positions 92 indicate the positions of the body surface marker 62 at the respective breathing phases calculated by the marker motion measurement module 84. The elements of the set of the gold marker positions 93 indicate the positions of the gold marker 63 at the respective breathing phase calculated by the marker motion measurement module 84. The elements of the set of affected part positions 94 indicate the positions of the affected part 61, and indicate the positions where the affected part 61 is positioned when the body surface marker 62 is arranged at the positions indicated by the elements of the set of the body surface marker positions 92 and the gold marker 63 is arranged at the positions indicated by the elements of the set of the gold marker positions 93.

That is, the irradiation control module 88 refers to the affected part position table 91 to calculate the affected part position corresponding to the positions of the body surface marker 62 and the position of the gold marker 63, the positions being collected by the marker position measurement module 86 from among the set of the affected part positions 94, drives the therapeutic radiation irradiation device 16 by using the oscillation mechanism 15 so that the therapeutic radiation 23 transmits through the affected part position, and controls the shape of the irradiation field of the therapeutic radiation 23 by using the MLC.

An embodiment of the radiation irradiation method according to the present invention is carried out by the radiation therapy apparatus control device 80, and includes: an operation for creating the affected part position table 91; and an operation for carrying out the radiation therapy.

Figure 9:
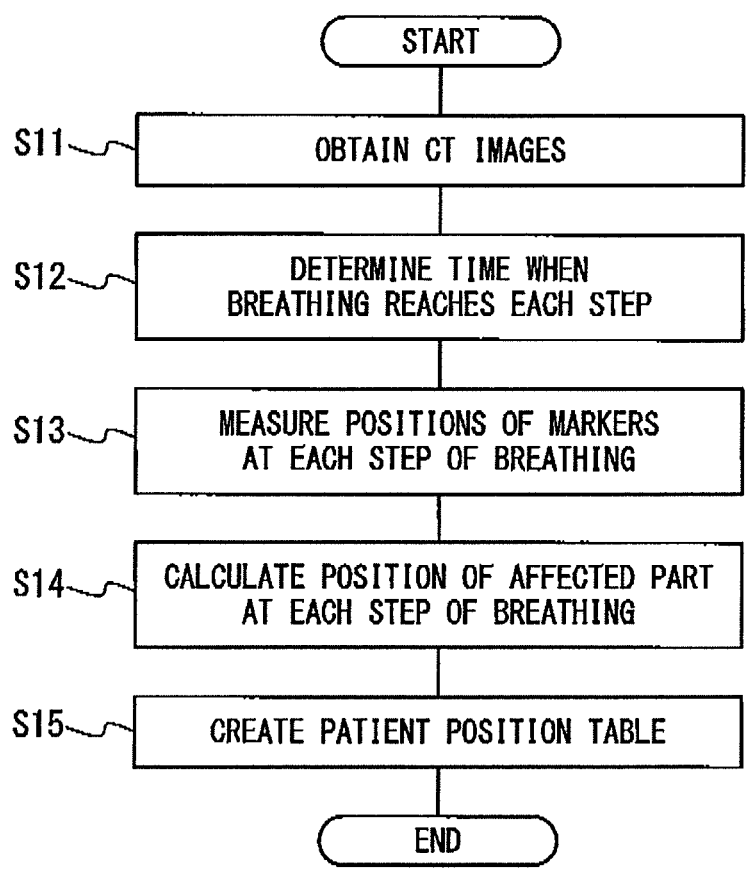
FIG. 9 is a flowchart showing an operation to create the patient position table.

FIG. 9 shows the operation for creating the affected part position table 91. At first, the user creates the three-dimensional data of: the affected part of the patient 43; and the portion around the affected part by using the computer tomography imaging device 5 (Step S11). The radiation therapy apparatus control device 80 generates an image showing the affected part of the patient 43 and the portion around the affected part on the basis of the three-dimensional data generated by the computer tomography imaging device 5, and shows the image on the display. The user views the image by using the radiation therapy apparatus control device 80, and inputs data indicating the contour of the region in which the affected part 61 is shown in the image to the radiation therapy apparatus control device 80. The radiation therapy apparatus control device 80 calculates the position of the affected part 61 on the basis of the data.

Moreover, the user fixes the patient 43 on the couch 41 of the radiation therapy apparatus 3 so that the patient 43 can take the same stance as that of the case where the three-dimensional data has been obtained by using the computer tomography imaging device 5, and sets the spirometer 4 so that the breathing of the patient 43 can be observed. The radiation therapy apparatus control device 80 collects the ventilation volume from the spirometer 4, and based on the ventilation volume, detects the times at which the breathing reaches the respective steps (Step S12). The radiation therapy apparatus control device 80 images infrared images of the patient 43 by using the infrared camera 6, detecting the breathing phase by using the spirometer 4. Moreover, the radiation therapy apparatus control device 80 irradiates the patient 43 with the diagnostic X-ray 35 by using the diagnostic X-ray source 24, detecting the breathing phase by using the spirometer 4, and images the transmission images of the affected part of the patient 43 by using the sensor array 32. Furthermore, the radiation therapy apparatus control device 80 emits the diagnostic X-ray 36 by using the diagnostic X-ray source 25, detecting the breathing phase by using the spirometer 4, and images the transmission images of the affected part of the patient 43 by using the sensor array 33.

Based on the infrared images, the radiation therapy apparatus control device 80 calculates how the body surface marker 62 moves in accordance with the breathing. That is, based on the infrared images, the radiation therapy apparatus control device 80 calculates the positions of the body surface marker 62 at the times at which the breathing reaches the respective steps.

Moreover, based on the transmission images, the radiation therapy apparatus control device 80 calculates how the gold marker 63 moves in accordance with the breathing. That is, based on the transmission images, the radiation therapy apparatus control device 80 calculates the positions of the gold marker 63 at the times at which the breathing reaches the respective steps (Step S13).

Based on the motion of the body surface marker 62 and the motion of the gold marker 63, the radiation therapy apparatus control device 80 calculates the motions of the portions of the patient 43 corresponding to the VOXELS 71-(0,0,0) to 71-(X,Y,Z), and calculates the positions of the portions of the patient 43 at each breathing phase (Step S14).

The radiation therapy apparatus control device 80 creates the affected part position table 91 and records the table into the storage device so that the position of the body surface marker 62 at each breathing phase and the position of the gold marker 63 at each breathing phase both calculated at Step S13 are correlated with the position of the affected part 61 at each breathing phase calculated at Step S14 (Step S15).

Figure 10:
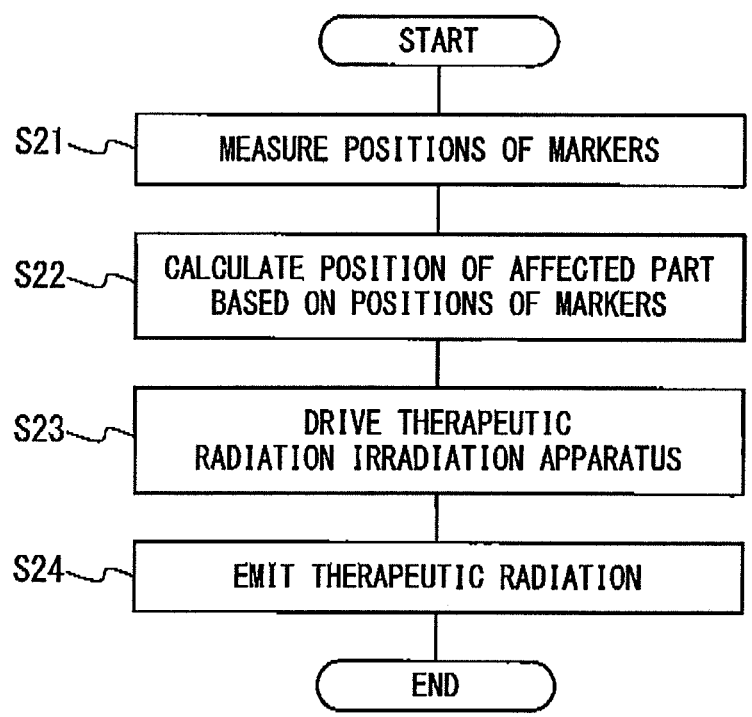
FIG. 10 is a flowchart showing an operation to implement a radiation therapy.

FIG. 10 shows the operation for carrying out the radiation therapy. At first, the user fixes the patient 43 on the couch 41 of the radiation therapy apparatus 3 so that the patient 43 can take the same stance as that of the case where the three-dimensional data has been obtained by using the computer tomography imaging device 5 or the imager system of the radiation therapy apparatus 3. The radiation therapy apparatus control device 80 emits the diagnostic X-ray 35 by using the diagnostic X-ray source 24, and images the transmission images of the patient 43 generated on the basis of the diagnostic X-ray 35 by using the sensor array 32. Moreover, the radiation therapy apparatus control device 80 emits the diagnostic X-ray 36 by using the diagnostic X-ray source 25; and images the transmission images of the patient 43 generated on the basis of the diagnostic X-ray 36 by using the sensor array 33. Based on the transmission images, the radiation therapy apparatus control device 80 calculates the positions of the gold marker 63. Moreover, the radiation therapy apparatus control device 80 sequentially obtains infrared images by using the infrared camera 6, with the infrared images of the patient 43 correlated with the imaging times, and calculates the positions of the body surface marker 62 on the basis of the infrared images (Step S21).

Referring to the affected part position table 91, the radiation therapy apparatus control device 80 calculates the affected part position, which is related to the position of the body surface marker 62 and the position of the gold marker 63 both calculated at Step S21 from among the set of the affected part positions (Step S22). The radiation therapy apparatus control device 80 drives the therapeutic radiation irradiation device 16 by using the oscillation mechanism 15 so that the therapeutic radiation 23 passes through the affected part position, and controls the shape of the irradiation field of the therapeutic radiation 23 by using the MLC (Step S23). The radiation therapy apparatus control device 80 irradiates the affected part with the therapeutic radiation 23 by using the therapeutic radiation irradiation device 16 immediately after the therapeutic radiation irradiation device 16 has moved by the tracking operation (Step S24). The radiation therapy apparatus control device 80 carries out the radiation therapy to the patient 43 by periodically repeating the operations from Step S21 to Step S24.

This radiation irradiation method only requires generation of the three-dimensional data at a specific timing by using the computer tomography imaging device 5 in a case where the position correction tracking irradiation or the shape correction tracking irradiation is applied, and the dose of radiation with which the patient 43 is irradiated can be more reduced in calculating the motion of the affected part 61 of the patient 43 in comparison with a case when the motion of the plurality of portions of the patient 43 is calculated on the basis of information measured by the 4D-CT.

Generally, the three-dimensional data detected by the 4D-CT has a rough time resolution, and it is difficult to make the time resolution be more accurate than the breathing phase divided by using the spirometer 4. Furthermore, according to this radiation irradiation method, the time resolution to detect the motions of the markers can be improved more easily in comparison with the 4D-CT, and on this occasion, the affected part 61 of the patient 43 can be irradiated with the therapeutic radiation 23, more accurately.

In another embodiment of the radiation irradiation method according to the present invention, the operation at Step S22 in the above-mentioned embodiment is replaced by a different operation. In this operation, every when the position of the body surface marker 62 and the position of the gold marker 63 are calculated, the positions of the respective portions of the patient 43 are calculated on the basis of the position of the body surface marker 62, of the position of the gold marker 63, and of the three-dimensional data generated by the computer tomography imaging device 5 of the radiation therapy apparatus control device 80.

When the processing speed of the CPU of the radiation therapy apparatus control device 80 is fast enough to calculate the affected part position of the affected part 61 within a predetermined time from the input of the transmission image and the infrared image of the patient 43, this radiation irradiation method can be employed. According to this radiation irradiation method, in the same manner as that of the radiation irradiation method in the above-described embodiment, the dose of radiation irradiated to the patient 43 in calculating the position of the affected part 61 of the patient 43 can be reduced, and the affected part 61 of the patient 43 can be irradiated with the therapeutic radiation 23, more accurately. Moreover, this radiation irradiation method is preferable, since there is no need to create the affected part position table 91.

The radiation therapy planning apparatus and the radiation therapy planning method according to the present invention can calculate the dose of the therapeutic radiation with which the respective portions of the subject is irradiated in the radiation therapy, more accurately. Moreover, the radiation therapy planning apparatus and the radiation therapy planning method according to the present invention reduces the dose of radiation with which the subject is irradiated, in the case where the dose of the therapeutic radiation with which the respective portions of the subject is irradiated is calculated more accurately, that is, in the case where the motion of the subject in the irradiation of the therapeutic radiation is calculated.

The invention claimed is:

1. A radiation therapy planning apparatus, comprising:
a three-dimensional data collection part configured to collect three-dimensional data representing positions of a plurality of portions of a subject at a single specific timing;
a marker position measurement part configured to sequentially measure a specific position of a specific portion out of the plurality of portions, which changes in synchronization with periodic movement of the subject;
a position calculation part configured to calculate time-dependent specific positions of the plurality of portions based on the three-dimensional data representing the positions of the plurality of portions of the subject at the single specific timing, and on the time-dependent specific position measured by said marker position measurement part; and a dose calculation part configured to calculate a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions calculated by said position calculation part.

2. The radiation therapy planning apparatus according to claim 1, further comprising:
an irradiation recipe collection part including an irradiation recipe input device configured to have an irradiation recipe for irradiating the therapeutic radiation controlled so as to change based on the periodic motion of the subject inputted therein, and being configured to collect the irradiation recipe inputted to said irradiation recipe input device,
wherein said dose calculation part is configured to calculate a dose of the therapeutic radiation when controlled in accordance with the irradiation recipe which is inputted into said irradiation recipe input device and collected by said irradiation recipe collection part.

3. The radiation therapy planning apparatus according to claim 1, further comprising:
a phase detection part configured to detect a plurality of times corresponding to a plurality of phases of the periodic motion of the subject,
wherein the position of the single specific portion measured by said marker position measurement part indicates the position at the plurality of times detected by said phase detection part.

4. The radiation therapy planning apparatus according to claim 1, further comprising:
a selected portion input device to which data to select any one of the plurality of portions is configured to be inputted,
wherein said dose calculation part is further configured to calculate a dose of radiation with which the selected portion of the plurality of portions selected based on the data inputted to said selected portion input device is irradiated.

5. The radiation therapy planning apparatus according to claim 1, wherein said three-dimensional data collection part is configured to collect three-dimensional data that indicates positions of an affected part to be irradiated, a risky portion to be kept away from the irradiation, and a specific portion which is capable of being measured by said marker position measurement part, in the subject.

6. The radiation therapy planning apparatus according to claim 1, wherein said marker position measurement part is configured to measure the specific portion, the specific portion being a construction element of the subject, a marker on a body surface of the subject, or a marker inside a body of the subject, which is capable of being measured by said marker position measurement part.

7. The radiation therapy planning apparatus according to claim 1, wherein said position calculation part is configured to implement a calculation method based on a linear scaling in which such an estimation is carried out such that distances from a fixed portion for the subject to the plurality of portions are extended or shortened in accordance with an extending or shortening change of a distance from the fixed portion to the specific portion.

8. The radiation therapy planning apparatus according to claim 1, wherein said position calculation part is configured to implement a calculation method based on a simulation which estimates the positions of the plurality of portions by applying a simulation of a human body model in which a fixed portion for the subject and the position of the specific portion are preliminarily configured.

9. A radiation therapy planning method, comprising:
collecting three-dimensional data representing a plurality of positions of a plurality of portions of a subject a single specific timing;
sequentially measuring a specific position of a specific portion out of the plurality of portions which changes in synchronization with periodic movement of the subject;
calculating time-dependent specific positions of the plurality of portions based on the three-dimensional data representing the positions of the plurality of portions of the subject at the single specific timing, and the time-dependent specific position measured by a marker position measurement part; and
calculating a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions.

10. The radiation therapy planning method according to claim 9, further comprising:
collecting from an irradiation recipe input device an irradiation recipe for irradiating the therapeutic radiation controlled so as to change based on the periodic motion of the subject; and
calculating a dose of the therapeutic radiation when controlled in accordance with the irradiation recipe.

11. The radiation therapy planning method according to claim 9, further comprising:
detecting a plurality of times corresponding to a plurality of phases of the periodic motion of the subject,
wherein the position of the specific portion indicates the position at the plurality of times.

12. The radiation therapy planning method according to claim 9, further comprising:
further calculating a dose of radiation with which the selected portion of the plurality of portions selected based on data inputted to a selected portion input device is irradiated.

13. The radiation therapy planning method according to claim 9, wherein the three-dimensional data indicate positions of an affected part to be irradiated, a risky portion that is to avoid the irradiation, and a specific portion which is capable of being measured by the marker position measurement part, in the subject.

14. The radiation therapy planning method according to claim 9, wherein the specific portion is a construction element of the subject, a marker on a body surface of the subject, or a marker inside a body of the subject.

15. The radiation therapy planning method according to claim 9, wherein the positions of the plurality of portions are calculated by a linear scaling in which an estimation is carried out that distances from a fixed portion for the subject to the plurality of portions are extended or shortened in accordance with an extending or shortening change of a distance from the fixed portion to the specific portion.

16. The radiation therapy planning method according to claim 9, wherein the positions of the plurality of portions are calculated by a simulation method which estimates the positions of the plurality of portions by applying a simulation of a human body model in which a fixed portion for the subject and the position of the specific portion are preliminarily configured.

17. A radiation therapy apparatus control device, comprising:
- a three-dimensional data collection part configured to collect three-dimensional data representing positions of a plurality of portions of a subject at a single specific timing;
- a marker position measurement part configured to measure a specific position of a specific portion of the plurality of portions;
- a position calculation part configured to calculate an irradiation position of an irradiation portion of the plurality of portions based on the three-dimensional data representing the positions of the plurality of portions of the subject at the single specific timing and the specific position; and
- an irradiation control part configured to move a therapeutic radiation irradiation device by using a drive device so that the irradiation position is irradiated with therapeutic radiation.

18. The radiation therapy apparatus control device according to claim 17, wherein said position calculation part is configured to calculate the irradiation position by using a linear scaling for carrying out an estimation that a distance from a substantially fixed portion out of the plurality of portions to each of the plurality of portions is extended or shortened in accordance with an extending or shortening change of a distance from the fixed portion to the specific portion.

19. The radiation therapy apparatus control device according to claim 17, further comprising:
- a marker motion measurement part configured to measure a motion of the specific portion to generate motion data indicating the motion; and
- an affected part position table creation part configured to create an affected part position table that correlates a set of specific position motions with a set of positions, based on the three-dimensional data and the motion data,
- wherein said position calculation part is configured to refer to the affected part position table to calculate the irradiation position corresponding to the specific position out of the set of positions.

20. The radiation therapy apparatus control device according to claim 17, further comprising:
- a phase detection part configured to detect a plurality of times corresponding to a plurality of phases of a periodic motion of the subject,
- wherein the set of positions indicate positions of the specific portion at the plurality of times.

21. A radiation therapy planning apparatus, comprising:
- a three-dimensional data collection part configured to collect three-dimensional data representing positions of a plurality of portions of a subject at a single specific timing;
- a marker position measurement part configured to sequentially measure a specific position of a specific portion out of the plurality of portions which changes in synchronization with periodic movement of the subject;
- a position calculation part configured to calculate motion of the plurality of portions by time-dependently evolving positions of the plurality of portions described in the three-dimensional data representing the positions of the plurality of portions of the subject at a specific timing, based on the single specific timing collected by said three-dimensional data collection part and on the time-dependent specific position measured by said marker position measurement part; and
- a dose calculation part configured to calculate a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the motion of the plurality of portions calculated by the position calculation part.

22. The radiation therapy planning apparatus according to claim 21, wherein said dose calculation part is configured to calculate a dose of radiation based on the motion of the plurality of portions which represents positions of the plurality of portions in respective phases of breathing.

23. A radiation therapy planning apparatus, comprising:
- a three-dimensional data collection part configured to collect three-dimensional data representing positions of a plurality of portions of a subject at a single specific timing;
- a marker position measurement part configured to sequentially measure a motion of a first marker disposed on a body surface of the subject out of the plurality of portions which changes in synchronization with a periodic movement of subject and a motion of a second marker disposed in the subject out of the plurality of portions;
- a position calculation part configured to calculate motion of the plurality of portions by time-dependently evolving positions of the plurality of portions described in the three-dimensional data representing the positions of the plurality of portions of the subject at the single specific timing, based on the single specific timing collected by the three-dimensional data collection part, on the motions of the first and second markers measured by said marker position measurement part and on the time-dependent specific position measured by the marker position measurement part; and
- a dose calculation part configured to calculate a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the motion of the plurality of portions calculated by said position calculation part.

24. A radiation therapy planning apparatus, comprising:
- a three-dimensional data collection part configured to collect three-dimensional data representing a plurality of positions where a plurality of portions of a subject are positioned in a stationary state or a state at a specific timing;
- a marker position measurement part configured to sequentially measure a specific position of a specific portion out of the plurality of portions which changes in synchronization with a periodic movement of the subject;
- a position calculation part configured to calculate time-dependent specific positions of the plurality of portions based on the three-dimensional data collected by said three-dimensional data collection part and on the time-dependent specific position measured by said marker position measurement part; and
- a dose calculation part configured to calculate a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions calculated by said position calculation part,
- wherein a calculation method implemented in said position calculation part is based on a linear scaling in which an estimation is carried out that distances from a fixed portion in contact with a couch of the subject to the plurality of portions are extended or shortened in accordance with an extending or shortening change of a distance from the fixed portion to the specific portion.

25. A radiation therapy planning apparatus, comprising:

a three-dimensional data collection part configured to collect three-dimensional data representing a plurality of positions where a plurality of portions of a subject are positioned in a stationary state or a state at a specific timing;

a marker position measurement part configured to sequentially measure a specific position of a specific portion out of the plurality of portions which changes in synchronization with a periodic movement of the subject;

a position calculation part calculating time-dependent specific positions of the plurality of portions based on the three-dimensional data collected by said three-dimensional data collection part and on the time-dependent specific position measured by said marker position measurement part; and a dose calculation part configured to calculate a dose of radiation with which each of the plurality of portions is irradiated, based on planned reference irradiation angles which are irradiation directions of therapeutic radiation, on a planned dose of the therapeutic radiation irradiated at each planned reference irradiation angle, and on the time-dependent positions of the plurality of portions calculated by said position calculation part, wherein a calculation method implemented in said position calculation part is based on a linear scaling in which such an estimation is carried out that distances from a pelvis or a backbone of the subject to the plurality of portions are extended or shortened in accordance with an extending or shortening change of a distance from the pelvis or backbone to the specific portion.

\* \* \* \* \*